(12) United States Patent
Chou et al.

(10) Patent No.: US 12,029,277 B2
(45) Date of Patent: Jul. 9, 2024

(54) INSOLE WITH EMBEDDED SENSING SYSTEM

(71) Applicants: Yao-Sheng Chou, Taipei (TW); Pai-Ching Wei, Tainan (TW)

(72) Inventors: Yao-Sheng Chou, Taipei (TW); Pai-Ching Wei, Tainan (TW)

(73) Assignee: Decentralized Biotechnology Intelligence Co., Ltd., Taipei (TW)

(*) Notice: Subject to any disclaimer, the term of this patent is extended or adjusted under 35 U.S.C. 154(b) by 435 days.

(21) Appl. No.: 17/516,635

(22) Filed: Nov. 1, 2021

(65) Prior Publication Data
US 2022/0408872 A1    Dec. 29, 2022

(30) Foreign Application Priority Data
Jun. 23, 2021   (TW) ................................ 110122982

(51) Int. Cl.
| A43B 3/34 | (2022.01) |
| A43B 17/02 | (2006.01) |
| A61B 5/00 | (2006.01) |
| A61B 5/103 | (2006.01) |

(52) U.S. Cl.
CPC ............... *A43B 3/34* (2022.01); *A43B 17/02* (2013.01); *A61B 5/1038* (2013.01); *A61B 5/6807* (2013.01); *A61B 2562/0219* (2013.01); *A61B 2562/0247* (2013.01)

(58) Field of Classification Search
CPC ........ A43B 3/34; A61B 5/1038; A61B 5/6807
USPC ......................................... 33/33 R, 3 B, 3 C
See application file for complete search history.

(56) References Cited

U.S. PATENT DOCUMENTS

| 6,195,921 | B1* | 3/2001 | Truong | .................... A43B 3/00 |
| | | | | 36/137 |
| 8,109,014 | B2* | 2/2012 | Miller | ....................... A43D 1/02 |
| | | | | 36/43 |
| 9,095,251 | B2* | 8/2015 | Purks | ....................... G01P 15/18 |
| 9,549,585 | B2* | 1/2017 | Amos | ........................ G01L 1/22 |
| 9,743,861 | B2* | 8/2017 | Giedwoyn | ............. G16H 20/30 |
| 10,219,726 | B2* | 3/2019 | Wei | ......................... A61B 5/112 |
| 10,660,402 | B2* | 5/2020 | Grimberg | ............... A43B 13/22 |
| 10,926,133 | B2* | 2/2021 | Giedwoyn | ......... A63B 24/0021 |
| 11,246,507 | B2* | 2/2022 | Markison | ............. A61B 5/1118 |
| 11,464,286 | B2* | 10/2022 | Jacob | ..................... A43B 13/20 |
| 11,871,814 | B2* | 1/2024 | Momokawa | ......... A61B 5/1036 |
| 2010/0000121 | A1* | 1/2010 | Brodie | .................... A43B 7/144 |
| | | | | 36/28 |
| 2016/0101571 | A1* | 4/2016 | Schouwenburg | ...... B33Y 50/00 |
| | | | | 602/5 |
| 2017/0188950 | A1* | 7/2017 | Gazdag | ................. G16H 20/30 |
| 2019/0139252 | A1* | 5/2019 | Zaiss | ....................... A43D 1/025 |
| 2023/0229284 | A1* | 7/2023 | Bicek | .................. G06F 3/04817 |
| 2024/0032642 | A1* | 2/2024 | Bock | ........................ A43B 3/44 |

* cited by examiner

*Primary Examiner* — George B Bennett

(57) ABSTRACT

An insole with embedded sensing system includes a pressure sensing layer arranged on the insole, an infrared sensing layer arranged inside the insole, and a sensing module installed inside an arch pad integrated with the insole. The sensing module is electrically coupled with the pressure sensing layer and the infrared sensing layer for receiving and processing detected electronic signals.

20 Claims, 6 Drawing Sheets

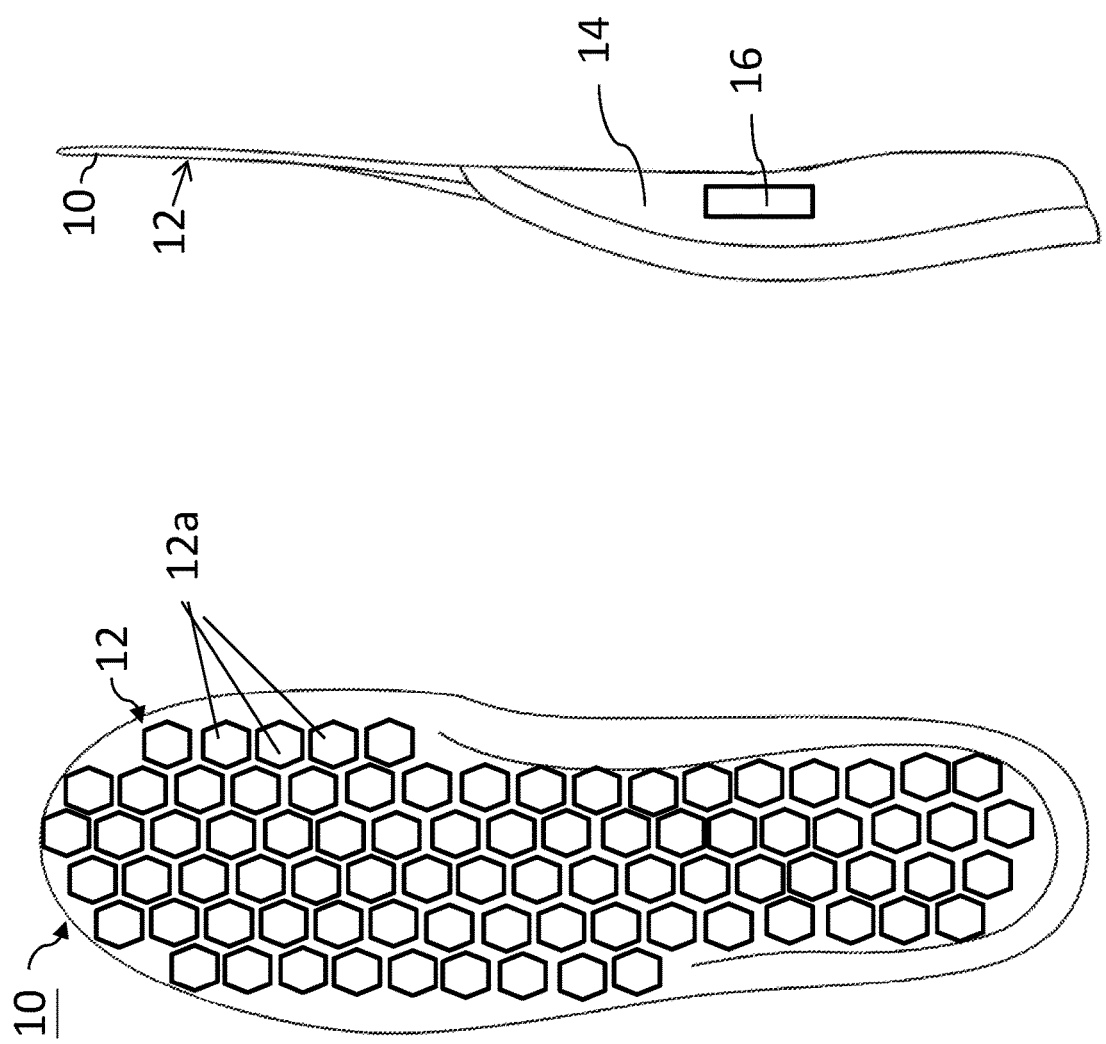

INSOLE WITH EMBEDDED SENSING SYSTEM

CROSS-REFERENCE TO RELATED APPLICATIONS

This patent application is based on, and claim priority from TAIWAN patent application serial number 110122982, filed on Jun. 23, 2021, the disclosure of which is hereby incorporated by reference herein in its' entirety.

TECHNICAL FIELD

The present invention relates to an insole, and more particularly, to an insole with embedded sensing system.

BACKGROUND OF RELATED ARTS

Recently, due to the development of electronic technology and information and communication technology, the field of health care has developed rapidly. That is, there is a need for a health management system that can measure the state of the human body through the usage of biological information.

The data of plantar pressure distribution can reveal the gait pattern of human body. The measurement of the plantar pressure distribution has great reference value in the fields of biomechanics, rehabilitation medicine, plastic surgery, sports training, shoe making and so on. At present, the clinical pressure test plate and technology of test bench have great space limitations and do not have wearability. Moreover, the test conditions and the measured pressure distribution are different from the actual pressure distribution when walking with shoes. Therefore, the present invention is proposed.

SUMMARY

Based on the above-mentioned, the development of wearable pressure shoes or pressure insoles has become an important work in the above fields. For example, a sensor for detecting pressure is configured in the shoe to check the wearer's health, walking posture, etc. When the pressure sensor is disposed into the sole or insole of the shoe, multiple other sensors are required and inserted into therein. Moreover, since some devices co-operated with the pressure sensor do not have flexibility and elasticity, it is difficult to set the whole sensing system on the insole with hyperboloid shape. Therefore, the following descriptions will explain how to overcome the above difficulties to achieve the purpose of the invention.

As an insole for testing plantar pressure, its pressure sensing unit needs to be in contact with human foot. In order to ensure the natural and comfortable state of human body in the testing process, the pressure sensing unit must be light, thin and soft. The configuration of other electronic components related to the pressure sensing unit needs to be considered separately.

The invention proposes an insole with embedded sensing system, comprising: a pressure sensing layer, configured on a surface of the insole; an Infrared sensing layer, configured within the insole; and a sensing module, configured in an arch support integrated with the insole, coupled to the pressure sensing layer and the Infrared sensing layer to receive and process electrical signals sensed by the pressure sensing layer and the Infrared sensing layer.

According to one aspect, the insole further comprises a mutual embedded structure to engage with an inner bottom of a shoe covered with the insole to avoid a relative displacement of the insole and the inner bottom of the shoe.

According to one aspect, the mutual embedded structure includes a plurality of bosses extending from a bottom of the insole to embed with a corresponding concave hole at the inner bottom of the shoe.

According to one aspect, the pressure sensing layer comprises a plurality of capacitive pressure sensors or resistive pressure sensors to form an array configuration, and the pressure sensing layer is flexible.

According to one aspect, the pressure sensing layer includes a plurality of capacitive sensors with different density distribution, which are arranged on a forefoot area, a lateral arch area and a heel area in said insole.

According to one aspect, the pressure sensing layer is flexible.

According to one aspect, the Infrared sensing layer is flexible.

According to one aspect, the sensing module provides program or algorithm to control collection and storage of data.

According to one aspect, the sensing module is configured to communicate with an external electronic device, which is an external computing device, a computing system, a mobile device, or other electronic device type.

According to one aspect, the sensing module comprises a processing unit to collect and analyze said electrical signals sensed by the pressure sensing layer and the Infrared sensing layer to convert the electrical signals to a corresponding foot pressure distribution and a blood circulation information; a memory coupled to the processing unit to store the corresponding foot pressure distribution and the blood circulation information; a wireless data transmission/receiving device coupled to the processing unit to transmit the corresponding foot pressure distribution and the blood circulation information to an external electrical device; and a power supply unit to provide power to the pressure sensing layer, the Infrared sensing layer, the processing unit, the memory and the wireless data transmission/receiving device.

According to one aspect, the wireless data transmission/receiving device is a Bluetooth chip or a WiFi (Wireless Fidelity) device.

BRIEF DESCRIPTION OF THE DRAWINGS

FIG. 1A shows a top view of an insole with a pressure detection function in accordance with one embodiment of the invention.

FIG. 1B shows a top view of an insole with a pressure detection function in accordance with one embodiment of the invention.

DETAILED DESCRIPTION

Figure 1D:
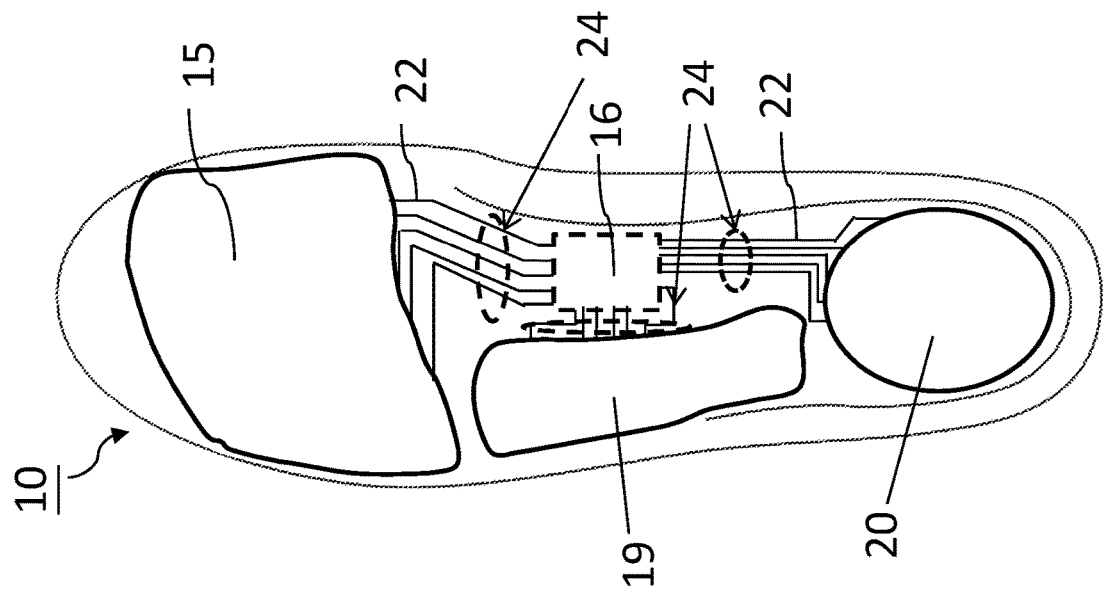
FIG. 1D shows a distribution diagram of pressure sensors and distributed lines in an insole with pressure detection function in accordance with one embodiment of the invention.

Some preferred embodiments of the present invention will now be described in greater detail. However, it should be recognized that the preferred embodiments of the present invention are provided for illustration rather than limiting the present invention. In addition, the present invention can be practiced in a wide range of other embodiments besides those explicitly described, and the scope of the present invention is not expressly limited except as specified in the accompanying claims.

Foot pressure distribution plays a critical role in a movement of human body. A posture of human body and changes in the bone are affected by foot shape and walking (running) posture, which also affects the performance and limit in sports. The invention provides an insole with a capacitive pressure sensing element and a built-in sensing system.

FIG. 1 shows an insole 10 with a pressure detection function according to an embodiment of the present invention. FIG. 1A shows a top view of the insole 10. The pressure sensing layer 12 is arranged on the surface of the insole. Generally speaking, the pressure sensing layer 12 is shaped for the foot of a user and is formed by network wiring (connection) in which a plurality of pressure sensors 12a form an array configuration. In a preferred embodiment, the pressure sensing layer 12 is flexible and formed by a plurality of capacitive pressure sensors (or resistive pressure sensors) 12a. Each pressure sensor 12a has a hexagon shape, triangle shape, circle shape or other shapes. Only the left insole is shown in the diagram. Here, it should be emphasized that the insole 10 is left-right pair. The right insole has exactly identical elements, devices, wiring methods, etc., as the left insole, and configured in a left-right symmetrical manner.

FIG. 1B shows a side view of the insole 10. The uppermost layer is the pressure sensing layer 12 (indicated by the arrow), on which there is an array configuration formed by a plurality of pressure sensors. An insole 10 is below the pressure sensing layer, which may include a thermoplastic polyester elastomer (TPEE) layer, and the insole 10 may also include an arch support (cushion) 14 integrated therein. A sensing module 16 used to collect, calculate, process and transmit the electronic signals of a plurality of pressure sensors is embedded in the arch support 14 of the insole, which can avoid or minimize the contact and stimulation to the wearer's foot.

Figure 1C:
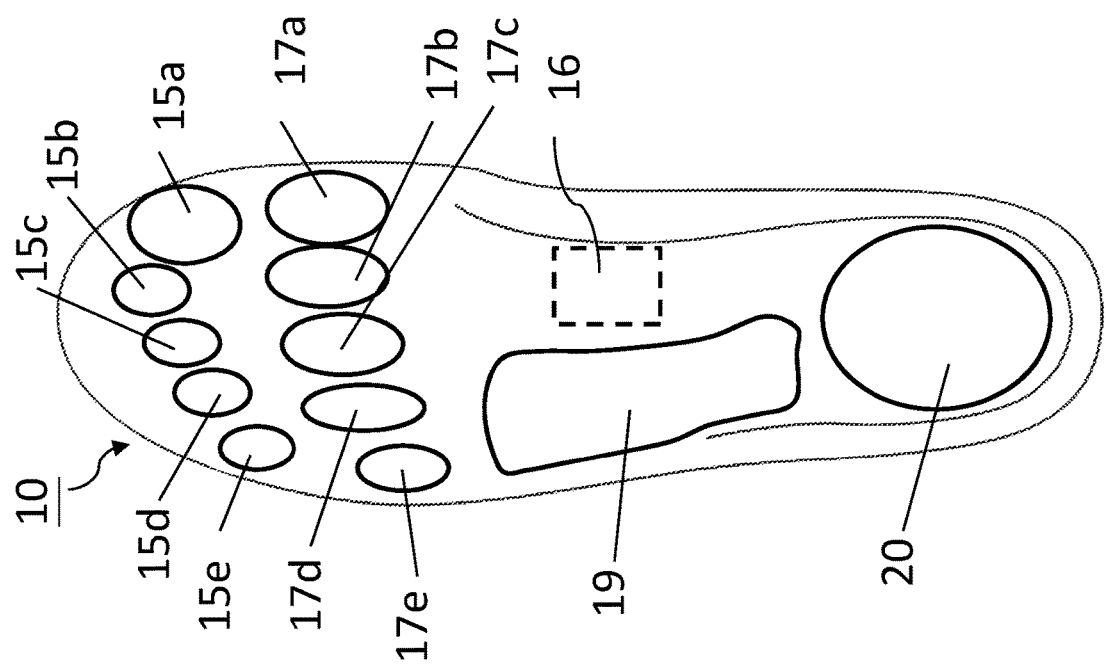
FIG. 1C shows a distribution diagram of pressure sensors in an insole with pressure detection function in accordance with one embodiment of the invention.

The pressure sensors on the pressure sensing layer, in addition to the configuration mode composed of network wiring in which a plurality of pressure sensors 12a form an array configuration as shown in FIG. 1A, the pressure sensors (not shown) can be distributed in different densities in the toe areas (15a, 15b, 15C, 15d, 15e), the forefoot areas (17a, 17b, 17c, 17d, 17e) lateral arch area 19 and heel area 20, i.e. plantar joint as shown in FIG. 1C. For detailed description, as shown in FIG. 1D, the pressure sensors (not shown) in the whole insole can be only configured at the positions in the toe area 15, the lateral arch area 19 and the heel area 20, wherein the pressure sensors can correspond to the positions of the toe areas (15a, 15b, 15c, 15d, 15e), the forefoot areas (17a, 17b, 17c, 17d, 17e), the lateral arch area 19 and the heel area 20 as shown in FIG. 1C. The pressure sensors (not shown) can be configured in different densities according to the requirements, and each of the pressure sensors is electrically connected to the sensing module 16 by wirings 22. In one embodiment, the pressure sensors are a capacitive pressure sensor, in which a plurality of capacitive pressure sensors with different numbers and corresponding wiring 24 form a flexible pressure sensing device, which is arranged in different parts of the insole to sense the foot pressure distribution of different areas (for example, the positions near the toe area 15, the lateral arch area 19 and the heel area 20) of the user's foot. In other words, the sensing densities of the above three areas are different, in which the density is in order from small to large: near toe area 15, lateral arch area 19 and heel area 20. Among them, the sensing module 16, including Bluetooth chip and other electronic components, is all embedded in the arch support 14 of the arch part of the insole 10. In one embodiment, the sensing module 16 may be an electronic sensing module integrated by a printed circuit board, which has a connection terminal electrically connected with the plurality of pressure sensing devices. The size of the sensing module 16 can be miniaturized, and its thickness is about 3~4.5 mm (millimeter).

Figure 1E:
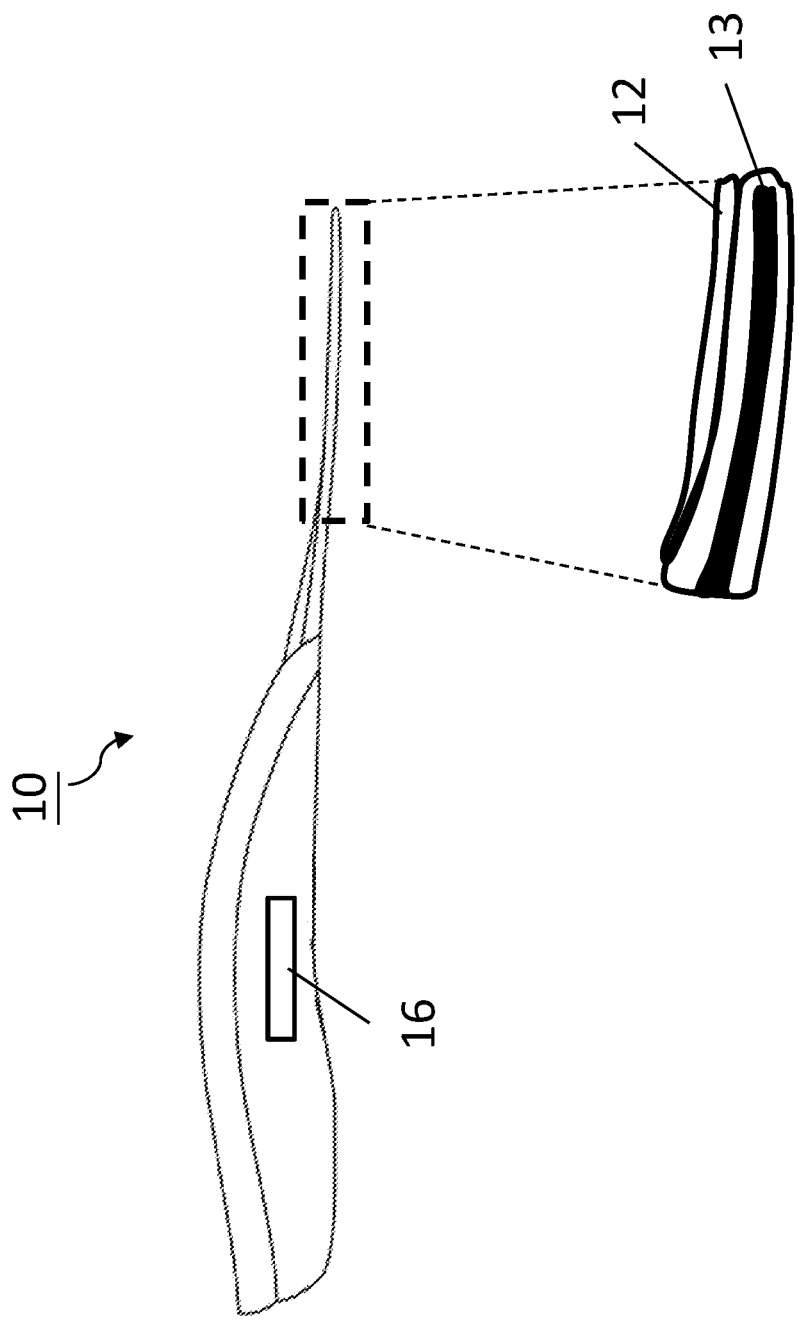
FIG. 1E shows a side view of an insole with a pressure detection function, integrated with an Infrared sensing layer in accordance with one embodiment of the invention.

In addition, the insole 10 can also integrate with an infrared sensor to detect the blood circulation of the user's foot. Based on the high penetration of infrared, the infrared sensor can detect the blood circulation of the foot without clinging to the human skin. FIG. 1E shows that an infrared sensing layer 13 includes a flexible infrared sensor and wiring, which is arranged inside the insole 10 to receive the infrared emitted from the human foot, and this configuration can avoid mutual interference with the pressure sensor. In one embodiment, the infrared sensing layer 13 can be electrically connected with the connection terminal of the sensing module 16 through the flexible wiring. Through the high penetration of the above infrared, the artery on the outside of the instep responsible for delivering blood to the foot is measured, so as to judge whether the instep pulse may be abnormal.

Figure 1F:
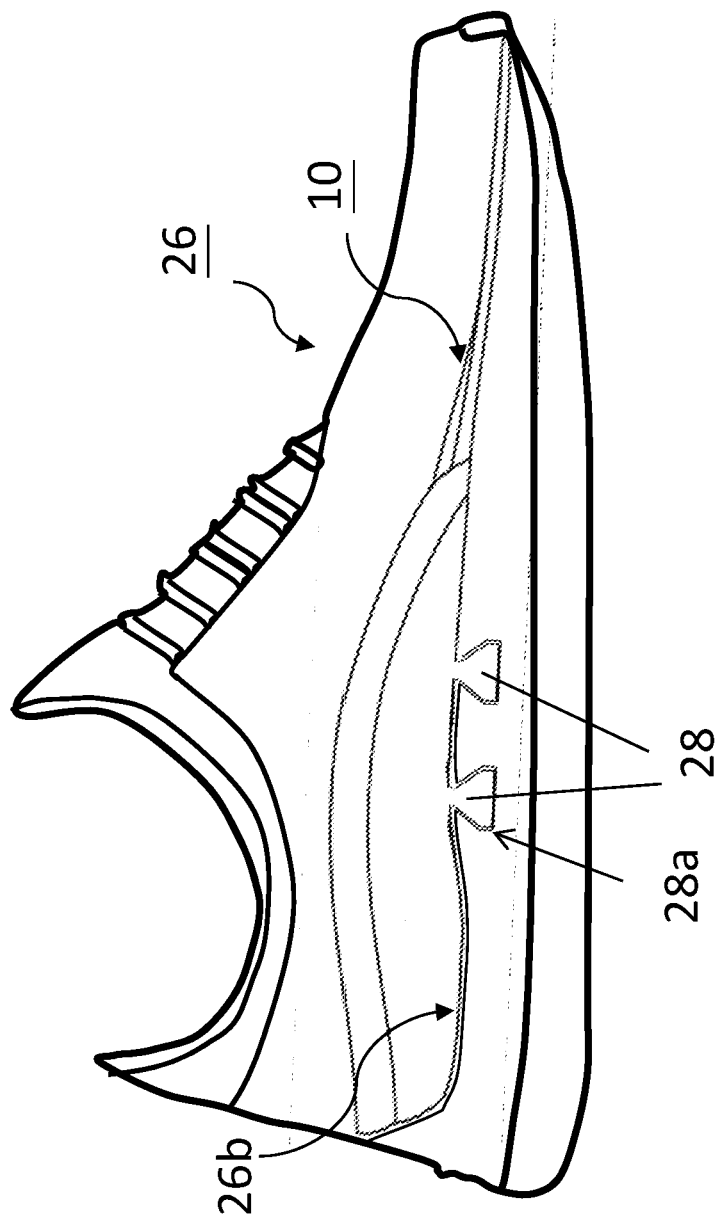
FIG. 1F shows a schematic diagram of an insole embedded with an inner bottom of a shoe in accordance with one embodiment of the invention.

Considering the measurement accuracy, the relative displacement of the insole 10 and the inner bottom 26b of the shoe 26 should be avoided as much as possible. Currently, it increases the friction between the bottom of the insole and the inner bottom of the shoe to overcome this issue, however, this method is not perfect. Therefore, the invention proposes a mutual embedded structure in which the insole and the inner bottom of the shoe are mutually embedded. As shown in FIG. 1F, a plurality of bosses (embossed portions) 28 can be designed at the bottom of the insole 10 to embed with the corresponding concave holes 28a at the inner bottom of the shoe, so that the relative displacement between the insole 10 and the inner bottom 26b can be avoided.

Figure 2:
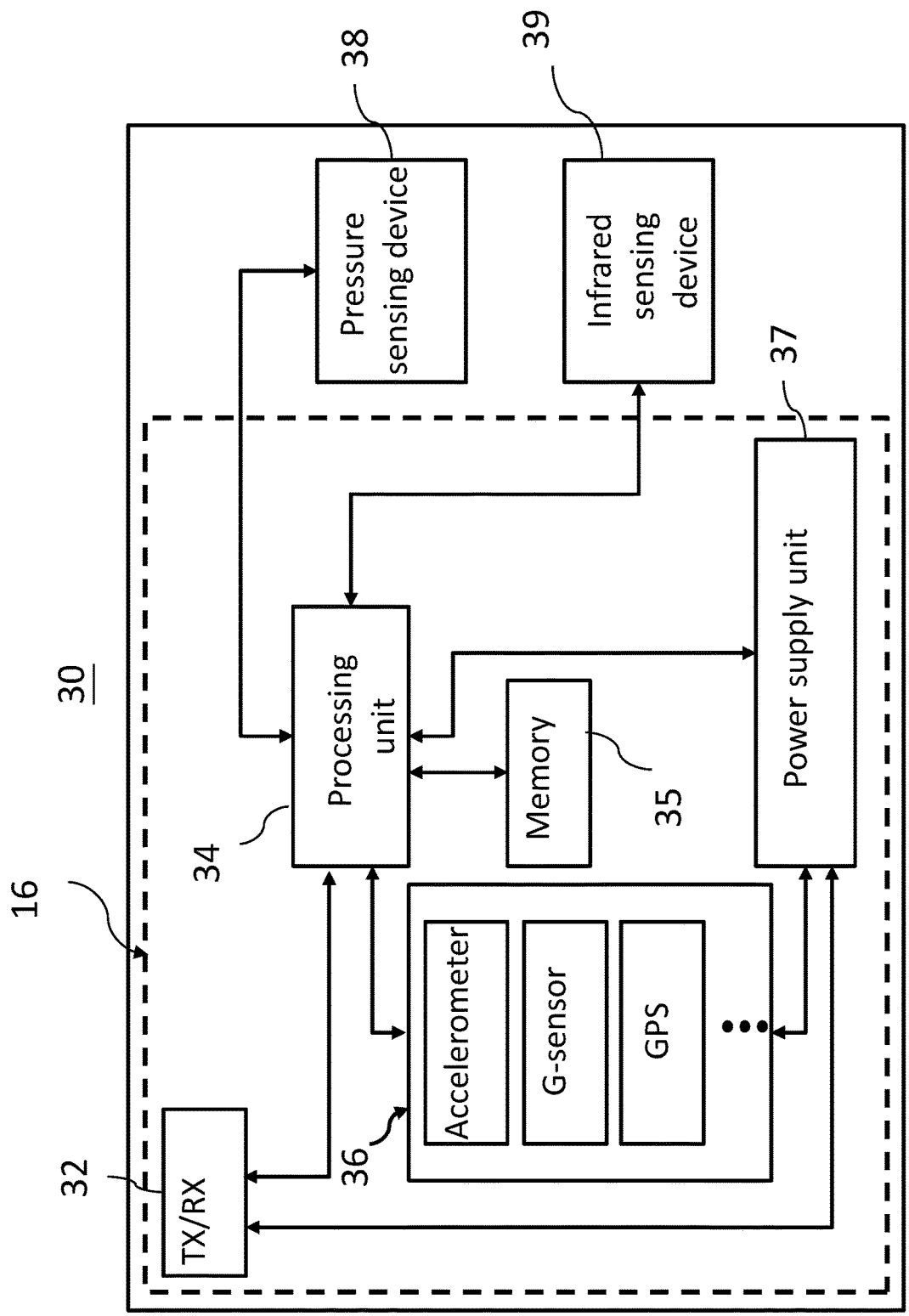
FIG. 2 shows a functional block diagram of an insole sensing system in accordance with one embodiment of the invention.

FIG. 2 shows a functional block diagram of an insole sensing system 30, which includes a sensing module 16 capable of data transmitting/receiving through a wireless data transmission/receiving device (TX/RX) 32. In FIG. 2, it shows that the wireless data transmission/receiving device (TX/RX) 32 is integrated into the sensing module 16, those skilled in the art can understand that the wireless data transmission/receiving device (TX/RX) 32 can also be a separate component for the purpose of data transmission/receiving. In the example of FIG. 2, the sensing module 16 includes a wireless data transmission/receiving device (TX/RX) 32 for transmitting data to and/or receiving data from one or more remote systems. In one embodiment, the wireless data transmission/receiving device (TX/RX) 32 may be a Bluetooth chip, WiFi (Wireless Fidelity) or similar wireless data transmission/receiving device. The sensing module 16 can be electrically connected with a plurality of pressure sensors (pressure sensing device 38) and an infrared sensing device 39 arranged on the insole via a connection terminal. The sensing module 16 also includes a processing unit 34 (such as, one or more microprocessors), a memory 35, additional sensors 36 (including accelerometer, gyroscope (G-sensor), Global Positioning System (GPS) sensor, etc.) 36, and a power supply unit 37. The proposed G-sensor is used for sensing the direction difference of each pace, sensing height difference, and/or correcting with each other as speed sensing compared with pressure sensing. The power supply unit 37 may supply power to the pressure sensing device 38, the infrared sensing device 39 and/or other components of the sensing system (such as, processing unit 34, memory 35, additional sensors 36, etc.). In a preferred embodiment, the power supply unit 37 includes a rechargeable solid-state battery, an inductive coil (for wireless charging the battery by coupling with an external wireless charging system) and a USB charging interface. It should be understood that the sensing module 16 can provide computing programs/algorithms to control the collection and storage of data (such as, pressure distribution data or pressure data interacting with the ground of user's foot, blood circulation status of user's foot, etc.), and these programs/algorithms can be stored and/or executed.

The TX/RX device 32 can completely connect to one or more sensors, and transmit or provide the detection data or information related to various different parameters created by the additional sensors 36. These data or information include physiological data related to the user, speed data/distance information of pedometer type, change of direction during walking detected by accelerometer, GPS data, acceleration output/data, angular orientation related data and change of angular orientation (sensing by G-sensor), and these data can be stored in the memory or transmitted to a remote computing device or server via the TX/RX device 32.

In the embodiment of FIG. 2, the sensing module 16 may include a startup system (not shown). That is, the system or a part thereof can be coupled to the sensing module 16 or connected to the insole or separated from other parts of the sensing module 16. The startup system may be used to selectively start the sensing module 16. In one embodiment, the sensing module 16 may be operated through a specified mode to enable the sensing module to be started or closed, such as a pressure threshold applied to one or more sensors. In other embodiments, the sensing module 16 may be turned on or off through a button. In any of these embodiments, the sensing module 16 may include a sleep mode that may put the system into the sleep mode after a period of inactive state. In one embodiment, for example, the G-sensor does not detect activity within a preset time, and the sensing module 16 may enter sleep mode to save power.

The sensing module 16 may also be configured to communicate with an external device, which may be an external computing device, a computing system, a mobile device (smart phone, tablet, etc.), or other electronic devices.

Figure 3:
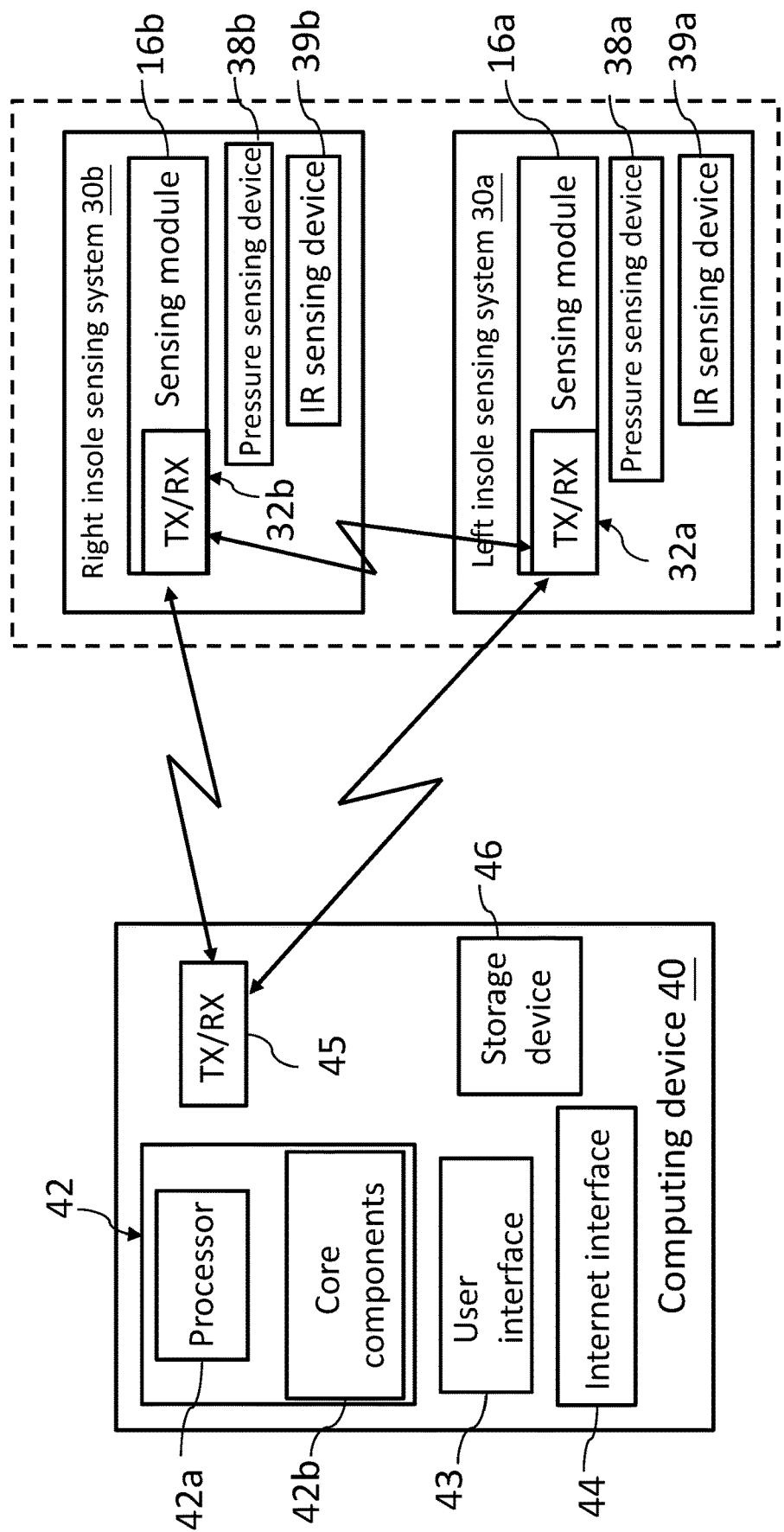
FIG. 3 shows a functional block diagram of a left and a right insole sensing system communicated with an external computing device in accordance with one embodiment of the invention.

FIG. 3 shows a system block diagram of communication between the left and right insole sensing systems (30a, 30b) and an external computing device 40. The left and right insole sensing systems (30a, 30b) each include a sensing module (16a, 16b) embedded in the arch of the insole, which is electrically connected with a pressure sensing devices (38a, 38b) and an infrared sensing device (39a, 39b) to receive and analyze a pressure distribution of the user's foot and a blood circulation data of foot, and transmit the above data to a remote computing device or server through a TX/RX device (32a, 32b) located in the sensing module. The sensing modules (16a, 16b) each include a processing unit (such as, one or more microprocessors), a memory, additional sensors, and a power supply unit (referring to FIG. 2).

The external computing device 40 is any electronic device that can transmit data, process data, and/or store data. In one embodiment, the computing device 40 is a portable computing device and/or a fixed computing device. The portable computing device may be a social network device, a game device, a mobile phone, a smart phone, a personal digital assistant, a digital audio/video player, a notebook computer, a tablet computer, a video game controller, and/or any other portable device containing a computing core. The fixed computing device may be a personal computer (PC), a computer server, a television, a printer, a fax machine, a home entertainment device, a video game console, and/or any type of home or office computing device containing a computing core.

The external computing device 40 includes a computing core 42, a user interface 43, an Internet interface 44, a wireless communication transceiver 45, and a storage device 46. The user interface 43 includes one or more input devices (such as, keyboard, touch screen, voice input device, etc.), one or more audio output devices (such as, speaker, headphone jack, etc.), and/or one or more video output devices (such as, video graphics display, touch screen, etc.). The Internet interface 44 includes one or more networking devices (such as, wireless local area network (WLAN) devices, wired LAN devices, wireless wide area network (WWAN) devices, etc.). The storage device 46 includes a flash memory device, one or more hard disk drives, one or more solid-state (SS) storage devices, and/or a cloud memory.

The computing core 42 includes a processor 42a and other computing core components 42b. Other computing core components 42b include a video graphics processing unit, a memory controller, a main memory (such as RAM), one or more input/output (I/O) device interface modules, input/output (I/O) interfaces, input/output (I/O) controllers, peripheral device interfaces, one or more USB interface modules, one or more network interface modules, one or more memory interface modules and/or one or more peripheral device interface modules.

The wireless communication transceiver 45 of the external computing device 40 and the wireless data transmission/receiving devices (32a, 32b) of the insole sensing system 30 have similar transceiver types (such as, Bluetooth, WLAN, WiFi, etc.). The wireless data transmission/receiving devices (32a, 32b) communicate directly with the wireless communication transceiver 45 to share the collected data and/or receive instructions from the external computing device 40 through the respective insole sensing system 30. In addition or as an alternative example, the wireless data transmission/receiving devices (32a, 32b) communicate with one of them to collect data. The wireless data transmission/receiving device 32a transmits the collective data to the wireless communication transceiver 45 of the external computing device 40.

The external computing device 40 processes data to produce various results. For example, the external computing device 40 processes the data from the sensing system 16 in combination with the circuit of algorithm, which can analyze any data related to foot pressure during movement, such as the pressure distribution on the wearer's left and right feet, the ratio of weight to the left and right feet, gait, gait frequency, and the center of pressure (COP) during body dynamics.

Foot pressure distribution plays a critical role in a movement of human body. A posture of human body and changes in the bone are affected by foot shape and walking (running) posture, which also affects the performance and limit in sports. The invention proposes an insole with built-in sensing system which can obtain the parameter data of foot pressure distribution of many users for time and space through the insole arranged in the shoe, and upload the data to external computing devices (e.g. smart phone, personal computer, computer servers, etc.) to calculate, analyze and store the data in the cloud system as relevant database of big data. In addition, the insole with a built-in sensing system can also integrate an infrared detection device to synchronously provide the user's blood circulation information. Breaking through the limitation that only medical institutions or sports research institutions can obtain data analysis in the past, the invention can facilitate more sports and more users obtaining exclusive movement or motion analysis. Synchronously, it also enables the establishment and use of data platforms in various professional fields, so that different professional fields (such as sports, health care, shoemaking, etc.) can establish their linkage relationship with foot pressure performance.

As will be understood by persons skilled in the art, the foregoing preferred embodiment of the present invention illustrates the present invention rather than limiting the present invention. Having described the invention in connection with a preferred embodiment, modifications will be suggested to those skilled in the art. Thus, the invention is not to be limited to this embodiment, but rather the invention is intended to cover various modifications and similar arrangements included within the spirit and scope of the appended claims, the scope of which should be accorded the broadest interpretation, thereby encompassing all such modifications and similar structures. While the preferred embodiment of the invention has been illustrated and described, it will be appreciated that various changes can be made without departing from the spirit and scope of the invention.

What is claimed is:

1. An insole with embedded sensing system, comprising:
    a pressure sensing layer, configured on a surface of said insole;
    an Infrared sensing layer, configured within said insole; and
    a sensing module, configured in an arch support integrated with said insole, coupled to said pressure sensing layer and said Infrared sensing layer to receive and process electrical signals sensed by said pressure sensing layer and said Infrared sensing layer.

2. The insole of claim 1, further comprising a mutual embedded structure to engage with an inner bottom of a shoe covered with said insole.

3. The insole of claim 2, wherein said mutual embedded structure includes a plurality of bosses extending from a bottom of said insole to embed with a corresponding concave hole at said inner bottom of said shoe.

4. The insole of claim 1, wherein said pressure sensing layer comprises a plurality of capacitive pressure sensors or resistive pressure sensors.

5. The insole of claim 1, wherein said pressure sensing layer is flexible.

6. The insole of claim 1, wherein said pressure sensing layer includes a plurality of capacitive sensors with different density distribution, which are arranged on a forefoot area, a lateral arch area and a heel area in said insole.

7. The insole of claim 6, wherein said pressure sensing layer is flexible.

8. The insole of claim 1, wherein said Infrared sensing layer is flexible.

9. The insole of claim 1, wherein said sensing module provides program or algorithm to control collection and storage of data.

10. The insole of claim 1, further comprising an accelerometer, a gyroscope (G-sensor) or a Global Positioning System (GPS) sensor.

11. An insole with embedded sensing system, comprising:
    a pressure sensing layer, configured on a surface of said insole;
    an Infrared sensing layer, configured within said insole; and
    a sensing module, configured in an arch support integrated with said insole, coupled to said pressure sensing layer and said Infrared sensing layer to receive and process electrical signals sensed by said pressure sensing layer and said Infrared sensing layer;
    wherein said sensing module includes:
    a processing unit to collect and analyze said electrical signals sensed by said pressure sensing layer and said Infrared sensing layer to convert said electrical signals to a corresponding foot pressure distribution and a blood circulation information;
    a memory coupled to said processing unit to store said corresponding foot pressure distribution and said blood circulation information;
    a wireless data transmission/receiving device coupled to said processing unit to transmit said corresponding foot pressure distribution and said blood circulation information to an external electrical device.

12. The insole of claim 11, further comprising a mutual embedded structure to engage with an inner bottom of a shoe covered with said insole.

13. The insole of claim 12, wherein said mutual embedded structure includes a plurality of bosses extending from a bottom of said insole to embed with a corresponding concave hole at said inner bottom of said shoe.

14. The insole of claim 11, wherein said pressure sensing layer comprises a plurality of capacitive pressure sensors or resistive pressure sensors.

15. The insole of claim 11, wherein said pressure sensing layer is flexible.

16. The insole of claim 11, wherein said pressure sensing layer includes a plurality of capacitive sensors with different density distribution, which are arranged on a forefoot area, a lateral arch area and a heel area in said insole.

17. The insole of claim 11, further comprising an accelerometer, a gyroscope (G-sensor) or a Global Positioning System (GPS) sensor.

18. The insole of claim 11, wherein said Infrared sensing layer is flexible.

19. The insole of claim 11, further comprising a power supply unit to provide power to said pressure sensing layer, said Infrared sensing layer, said processing unit, said memory and said wireless data transmission/receiving device.

20. The insole of claim 11, wherein said wireless data transmission/receiving device is a Bluetooth chip or a WiFi (Wireless Fidelity) device.

* * * * *